(12) United States Patent
McWeeney et al.

(10) Patent No.: US 10,182,798 B2
(45) Date of Patent: *Jan. 22, 2019

(54) EXCHANGEABLE CORE BIOPSY NEEDLE

(71) Applicant: COVIDIEN LP, Mansfield, MA (US)

(72) Inventors: John O. McWeeney, Brighton, MA (US); Stephen Tully, Waltham, MA (US); Eugene Campbell, Natick, MA (US); Bora Gumustop, Slingerlands, NY (US); Brian Tinkham, Sciterate, MA (US)

(73) Assignee: COVIDIEN LP, Mansfield, MA (US)

( * ) Notice: Subject to any disclaimer, the term of this patent is extended or adjusted under 35 U.S.C. 154(b) by 600 days.

This patent is subject to a terminal disclaimer.

(21) Appl. No.: 14/802,100

(22) Filed: Jul. 17, 2015

(65) Prior Publication Data

US 2016/0030018 A1    Feb. 4, 2016

Related U.S. Application Data

(60) Provisional application No. 62/030,828, filed on Jul. 30, 2014, provisional application No. 62/030,841, filed on Jul. 30, 2014.

(51) Int. Cl.
*A61B 10/02* (2006.01)
(52) U.S. Cl.
CPC .............................. *A61B 10/0275* (2013.01)
(58) Field of Classification Search
CPC ............ A61B 10/0266; A61B 10/0233; A61B 2017/3454
See application file for complete search history.

(56) References Cited

U.S. PATENT DOCUMENTS

| 4,708,147 A | 11/1987 | Haaga |
| 4,850,354 A | 7/1989 | McGurk-Burleson |

(Continued)

FOREIGN PATENT DOCUMENTS

| CN | 2126050 U | 12/1992 |
| CN | 2176117 Y | 9/1994 |

(Continued)

OTHER PUBLICATIONS

Notice of Reasons for Rejection for Japanese Patent Application No. 2015-148633, dated Aug. 3, 2016, from the Japanese Patent Office.
(Continued)

*Primary Examiner* — Sean Dougherty
*Assistant Examiner* — Nicholas E Kolderman

(57) ABSTRACT

The present disclosure provides an adjustable delivery handle system for interchangeably delivering a needle to a biopsy site. The adjustable delivery handle system includes a delivery handle having an inner hub housing component configured to interchangeably receive a needle subassembly that can be inserted into and withdrawn from the proximal handle member. The needle subassembly includes a biopsy needle having a distinct tissue collection distal end configured to maximize tissue sampling yield and collect a cohesive unit of sampled tissue. The distal end of the needle includes first and second tip portions extending therefrom and radially opposing one another. The first tip portion has a length greater than the second tip portion, thereby resulting in an increased surface area of a curvilinear cutting edge extending from the first tip portion to the second tip portion.

16 Claims, 9 Drawing Sheets

(56) References Cited

U.S. PATENT DOCUMENTS

| | | |
|---|---|---|
| 4,983,179 A | 1/1991 | Sjostrom |
| 5,313,958 A | 5/1994 | Bauer |
| 5,536,259 A | 7/1996 | Utterberg |
| 5,615,690 A | 4/1997 | Giurtino |
| 5,733,266 A | 3/1998 | Gravlee, Jr. |
| 5,746,724 A | 5/1998 | Powles et al. |
| 5,752,923 A | 5/1998 | Terwilliger |
| 5,752,942 A | 5/1998 | Doyle et al. |
| 5,810,788 A | 9/1998 | Racz |
| 5,817,033 A | 10/1998 | DeSantis et al. |
| 5,868,684 A | 2/1999 | Åkerfeldt et al. |
| 5,968,022 A | 10/1999 | Saito |
| 5,971,939 A | 10/1999 | DeSantis et al. |
| 6,009,933 A | 1/2000 | Doyle |
| 6,027,458 A | 2/2000 | Janssens |
| 6,027,514 A | 2/2000 | Stine |
| 6,213,989 B1 | 4/2001 | Utterberg |
| 6,315,737 B1 | 11/2001 | Skinner |
| 6,702,790 B1 | 3/2004 | Ross et al. |
| 6,752,769 B2 | 6/2004 | Alberico |
| 6,890,308 B2 | 5/2005 | Islam |
| RE38,776 E | 8/2005 | Bauer |
| 6,945,964 B2 | 9/2005 | Ross et al. |
| 7,008,381 B2 | 3/2006 | Janssens |
| 7,018,343 B2 | 3/2006 | Plishka |
| 7,070,583 B1 | 7/2006 | Higuchi et al. |
| 7,320,683 B2 | 1/2008 | Prais et al. |
| 7,455,645 B2 | 11/2008 | Goldenberg |
| 7,468,055 B2 | 12/2008 | Prais et al. |
| 7,470,249 B2 | 12/2008 | Junger |
| 7,591,807 B2 | 9/2009 | Villette |
| 7,645,268 B2 | 1/2010 | Mickley et al. |
| 7,731,667 B2 | 6/2010 | Goldenberg |
| 8,114,110 B2 | 2/2012 | Bednarek et al. |
| D657,461 S | 4/2012 | Schembre et al. |
| 8,317,727 B2 | 11/2012 | Peliks |
| 8,328,772 B2 | 12/2012 | Kinast et al. |
| 8,449,478 B2 | 5/2013 | Lee et al. |
| D690,009 S | 9/2013 | Schembre et al. |
| 8,568,422 B2 | 10/2013 | Morlet |
| 8,622,925 B2 | 1/2014 | Dunn |
| 8,728,005 B2 | 5/2014 | McClellan |
| 8,771,199 B2 | 7/2014 | Theobald et al. |
| 9,844,362 B2* | 12/2017 | McWeeney ........ A61B 10/0266 |
| 2006/0030785 A1 | 2/2006 | Field et al. |
| 2009/0018468 A1 | 1/2009 | Janssens |
| 2011/0224577 A1 | 9/2011 | Park |
| 2012/0010527 A1 | 1/2012 | Sundheimer et al. |
| 2012/0116248 A1* | 5/2012 | McWeeney ........ A61B 10/0283 |
| | | 600/567 |
| 2012/0130274 A1 | 5/2012 | Persat |
| 2012/0157880 A1 | 6/2012 | Haselby et al. |
| 2012/0165832 A1 | 6/2012 | Oostman, Jr. |
| 2012/0245486 A1 | 9/2012 | Melchiorri et al. |
| 2012/0253228 A1 | 10/2012 | Schembre et al. |
| 2012/0289985 A1* | 11/2012 | Motai ................ A61B 10/0233 |
| | | 606/185 |
| 2013/0041286 A1 | 2/2013 | Theobald et al. |
| 2013/0102925 A1 | 4/2013 | McGhie |
| 2013/0131547 A1 | 5/2013 | Hardert et al. |
| 2013/0131548 A1 | 5/2013 | McGhie et al. |
| 2015/0313580 A1 | 11/2015 | Dejima et al. |

FOREIGN PATENT DOCUMENTS

| | | |
|---|---|---|
| EP | 0221007 A1 | 5/1987 |
| EP | 2520237 A1 | 11/2012 |
| EP | 2982309 A1 | 2/2016 |
| JP | H07100140 A | 4/1995 |
| WO | 92/04062 A1 | 3/1992 |
| WO | 9508291 A1 | 3/1995 |
| WO | 9724070 A1 | 7/1997 |
| WO | 2004107984 A1 | 12/2004 |
| WO | 2011126963 A2 | 10/2011 |
| WO | 2013074653 A1 | 5/2013 |
| WO | 2014112518 A1 | 7/2014 |

OTHER PUBLICATIONS

Notice of Reasons for Rejection for Japanese Patent Application No. 2015-146692, dated Aug. 3, 2016, from the Japanese Patent Office.
Examination Report for EP Application No. 15178119.2, dated Jan. 17, 2017 from the European Patent Office.
Notification of the First Office Action from the State Intellectual Property Office of the People's Republic of China for Application No. 201510441591.0 dated Aug. 18, 2017.
Creganna Needle Brochure, published Jan. 16, 2008.
Extended European Search Report dated Jan. 11, 2015 in European application No. 15178119.2.
Chinese Office Action dated Feb. 6, 2016, for CN App. Model No. 201520562976.8, from the Chinese Patent Office.
EP extended European Search Report for Application No. 15178995.5 dated May 23, 2016, from the European Patent Office.
EP partial European search report for Application No. 15178995.5 dated Feb. 3, 2016, from the European Patent Office.
EP extended European search report for Application No. 15191407.4 dated Jun. 3, 2016 from the European Patent Office.
EP extended European search report for Application No. 15178119.2 dated Jan. 11, 2016 from the European Patent Office.
Chinese Office Action dated May 25, 2018, for CN App. Model No. 201510441591.0 from the Chinese Patent Office.

\* cited by examiner

SECTIONAL VIEW X-X

SECTIONAL VIEW Y-Y

EXCHANGEABLE CORE BIOPSY NEEDLE

CROSS-REFERENCE TO RELATED APPLICATIONS

This application claims the benefit of, and priority to, U.S. Provisional Patent Application Nos. 62/030,841 and 62/030,828, both of which were filed on Jul. 30, 2014. This application is related to U.S. patent application Ser. No. 14/802,039, filed on Jul. 17, 2015. The entire contents of each of the above applications are hereby incorporated herein by reference.

FIELD OF THE INVENTION

The present disclosure generally relates to biopsy devices, and, more particularly, to a biopsy needle configured for collecting tissue, fluid, and/or cell samples in conjunction with minimally-invasive procedures, such as endoscopic biopsy procedures.

BACKGROUND

In the practice of medical diagnostics, it is often necessary to perform a biopsy to remove a sample of a patient's tissue or fluid for pathological study. For example, biopsies can be useful in diagnosing various forms of cancer and other diseases affecting a localized area of tissue. Biopsy procedures may be used to take tissue and/or fluid samples from muscles, bones and organs, such as the liver or lungs. In some instances, a biopsy sample may be obtained by invasive surgical procedures. However, minimally invasive biopsy procedures are often preferred, such as fine needle aspiration and fine needle biopsy because such procedures are less traumatic to the patient.

Both fine needle aspiration (FNA) and fine needle biopsy (FNB) procedures generally include the use of a biopsy needle for collecting the target sample. FIGS. 1 and 2 are provided to illustrate one embodiment of a biopsy needle 100 currently available for use in biopsy procedures. As shown, the needle 100 includes a shaft 102 portion extending from a proximal end (not shown) to a distal cutting end 104 of the needle 100. The distal cutting end 104 includes a beveled leading end 106 resulting in a relatively sharp tip portion 110 used for puncturing the tissue to be sampled. The distal cutting end 104 of the needle 100 may be configured to cut and/or scrape target tissue to collect cells, tissue, or fragments. To sample the target area, the biopsy needle 100 may be guided to the tissue to be sampled through an instrument positioned in a patient. The instrument may be used with an endoscope, conduit and/or medical device insertion instrument. As shown, the needle 100 may be positioned within a sheath 108 of an endoscopic device, for example, such that the biopsy needle 100 may be retracted and extended from the sheath 108.

Upon contacting the tissue to be sampled (via the distal cutting end 104), the tissue sample may be collected within a lumen 112 of the shaft 102. In some devices, the needle 100 may extend from the sheath 108 and into the target tissue via a spring mechanism (not shown), such that the spring applies a force to the needle 100 and subsequently forces the distal cutting end 104 into the target tissue. Upon making contact with the target tissue, the distal cutting end 104 may separate a portion of the tissue from the surrounding tissue and collect the separated tissue within the lumen 112, which may result in a "core" sample (e.g., a number of intact adjacent cells held together in similar form to their native location). Additionally, or alternatively, suction may be applied to the proximal end of the needle 100 so as to aspirate the sample (e.g., cells, tissue, etc.) through the distal cutting end 104 of the needle 100 and into the lumen 112.

Generally, the goal of FNA and/or FNB is to acquire sufficient tissue to allow a diagnosis to be made. Currently, different needle tip configurations are used to collect different sample types (e.g., intact multi-cell samples useful for histology, cells and fragments useful for cytology, etc.). However, many existing biopsy needles are inefficient when collecting samples. For example, some needles use only about half or less of their inner diameter of the lumen to obtain tissue. Further, some current needle tip designs generally result in tearing of target tissue, which may result in a less than ideal core sample and unnecessary trauma to the surrounding tissue, which may cause further complications to the patient (e.g., internal bleeding, bruising, etc.) requiring further treatment.

Some devices that obtain a full cylinder or "full core" of tissue have difficulty in withdrawing tissue and/or in maintaining the physical state of the tissue so as to provide an accurate assessment of tissue condition. For example, some needles rely on scoring and/or mashing techniques during tissue collection, which may result in a damaged tissue sample. Depending on the diagnostics, physical characteristics of tissue, such as placement or orientation of cells or tissue, may be as important or more important than the chemical or biological characteristics (e.g. presence of malignant cells or by-products).

Furthermore, current needle tip designs may be insufficient for biopsy of certain types of tissue. For example, some lesions are particularly fibrous (e.g., pancreatic lesions) and are difficult to penetrate and obtain a suitable biopsy therefrom. Some bevel designs, such as the standard beveled cutting end of needle 100, may initially pierce a portion of the target lesion, but may then deflect off of or drift from the target lesion due to the inadequate tip design and/or inability to fully penetrate the lesion, which results in a poor tissue sample, and may even lead to damage to surrounding tissues or vital organs. Additionally, current bevel designs may merely shear off a portion of the target tissue and fail to collect some, or even all, of the sampled tissue within the lumen of the needle due to inadequate tip design.

SUMMARY

The present disclosure provides a biopsy needle configured to maximize tissue sampling yield and further ensure collection of a cohesive unit of sampled tissue, thereby overcoming the drawbacks of current biopsy needles, which either provide an insufficient amount of a sample for analysis and/or damage a sample during the collection process. The biopsy needle of the present disclosure is able to overcome the drawbacks of current needles by providing a distinct distal cutting end configured to collect a full core of tissue sample and keep the full core intact. More specifically, the distal end includes at least a first tip portion and a second tip portion that radially oppose one another on either side of the needle body. The first tip portion is longer than the second tip portion, resulting in an increase in the surface area of a cutting edge extending between the first and second tip portions, particularly when compared to the cutting surface of a beveled leading distal end of a conventional biopsy needle (e.g., see the needle of FIGS. 1 and 2). Additionally, because the first tip portion is longer than the second tip portion, the first tip portion is configured to initially pierce the tissue to be sampled with little or no resistance and further guide the sample tissue into the lumen of the biopsy needle. As the tissue is guided toward the lumen, second tip portion is further configured to capture and lead additional tissue towards the lumen to be excised by the cutting edge upon contact therewith. By increasing the effective cutting surface area and having the staggered configuration of first and second tip portions, the biopsy needle of the present disclosure is able to guide tissue into the lumen in a controlled manner and maximize the amount of tissue harvested, particularly upon aspiration.

In certain aspects, the present disclosure provides a biopsy needle that generally includes an elongate tubular body having a longitudinal axis and has a lumen extending therethrough from a proximal open end to a distal open end of the body. The distal end includes first and second tip portions extending therefrom. The first tip portion has a length greater than the second tip portion, such that the first tip portion is configured to contact and engage tissue to be sampled prior to the second tip portion.

In some embodiments, the first tip portion is formed from a first set of distinct angular bevel grinds oblique to the longitudinal axis of the body and the second tip portion is formed from a second set of distinct angular bevel grinds oblique to the longitudinal axis of the body. In some embodiments, the first set of angular bevel grinds includes first and second angles oblique to the longitudinal axis of the body and a back-cut angle oblique to an outer surface of the body for providing a smooth needle passage during needle insertion and withdrawal during a biopsy procedure. In some embodiments, the second set of angular bevel grinds includes third and fourth angles oblique to the longitudinal axis of the body. The first and second angles of the first set of angular bevel grinds may be less than the third and fourth angles of the second set of angular bevel grinds.

In some embodiments, the distal end further comprises at least one curvilinear cutting edge extending from the first tip portion to the second tip portion, wherein the cutting edge is configured to excise tissue upon contact therewith. Additionally, each of the first and second tip portions defines a point configured to pierce the tissue to be sampled and further direct tissue towards the lumen of the body to be excised by the cutting edge upon contact therewith.

The biopsy needle of the present disclosure may be used in conjunction with minimally-invasive procedures, such as endoscopic biopsy procedures. For example, the biopsy needle may be compatible with an endoscopic biopsy device, such as needle biopsy delivery device configured for endoscopic ultrasound or endoscopic bronchial ultrasound procedures.

In another aspect, the present disclosure includes a device for needle biopsy. The device includes an adjustable delivery handle system including a delivery handle, at least a portion of which comprises an inner lumen configured to receive one of a plurality of exchangeable needle subassemblies. The adjustable delivery handle system further includes a sheath coupled to a distal end of the handle and having a lumen in fluid communication with the inner lumen of the delivery handle. The device further includes a needle sub-assembly removably disposed within the inner lumen of the delivery handle and lumen of the sheath, the needle subassembly including an exchangeable biopsy needle. The biopsy needle generally includes an elongate tubular body having a longitudinal axis and has lumen extending therethrough from a proximal open end to a distal open end of the body. The distal end includes first and second tip portions extending therefrom. The first tip portion has a length greater than the second tip portion, such that the first tip portion is configured to contact and engage tissue to be sampled prior to the second tip portion.

In some embodiments, the first and second tip portions of the exchangeable needle radially oppose one another and are formed from first and second sets of distinct angular bevel grinds oblique to the longitudinal axis of the body, respectively. In some embodiments, the distal end of the exchangeable needle further comprises first and second curvilinear cutting edges radially opposing one another and extending from portions of the first tip portion to portions of the second tip portion. The cutting edges configured to excise tissue upon contact therewith. In some embodiments, the biopsy needle further comprises a collet surrounding a portion of the body and has a diameter sufficient to prevent the body from entirely passing through a distal end of the sheath of the adjustable delivery handle system.

DETAILED DESCRIPTION

By way of overview, the present disclosure is generally directed to a biopsy needle configured for collecting tissue, fluid, and/or cell samples in conjunction with minimally-invasive procedures, such as endoscopic biopsy procedures. As described in greater detail herein, a biopsy needle consistent with the present disclosure may be used in Endoscopic Ultrasound (EUS) and Endobronchial Ultrasound (EBUS) procedures, particularly EUS Fine Needle Aspiration (FNA), EUS Fine Needle Biopsy (FNB), EUS Coring, and EBUS procedures for the purpose of harvesting tissue specimen from a targeted site. It should be noted, however, that the biopsy needle may be used in other minimally-invasive procedures, and is not limited to EUS and/or EBUS procedures.

In one aspect, a biopsy needle consistent with the present disclosure includes an elongate tubular body having a longitudinal axis and a lumen extending therethrough from a proximal open end to a distal open end of the body. The distal end includes at least a first tip portion and a second tip portion that radially oppose one another on either side of the needle body. The first tip portion is longer than the second tip portion, resulting in an increase in the surface area of a cutting edge extending between the first and second tip portions, particularly when compared to the cutting surface of a beveled leading distal end of a conventional biopsy needle (e.g., see the needle of FIGS. 1 and 2).

Because the first tip portion is longer than the second tip portion, the first tip portion is configured to initially pierce the tissue to be sampled with little or no resistance and further guide the sample tissue into the lumen of the biopsy needle. As the tissue is guided toward the lumen, the second tip portion captures and leads additional tissue towards the lumen. During this process the tissue is excised by the cutting edge, creating a contiguous core biopsy sample. By increasing the effective cutting surface area and having the staggered configuration of first and second tip portions, the biopsy needle of the present disclosure is able to guide tissue into the lumen in a controlled manner and maximize the amount of tissue harvested, particularly upon aspiration.

The distinct distal cutting end of a biopsy needle consistent with the present disclosure is configured to collect a full core of tissue sample while keeping the full core intact. Accordingly, a biopsy needle consistent with the present disclosure is configured to maximize tissue sampling yield and further ensure collection of a cohesive unit of sampled tissue so as to provide a more complete sample for testing, which may improve the accuracy and/or timing of diagnosis.

Figure 3:
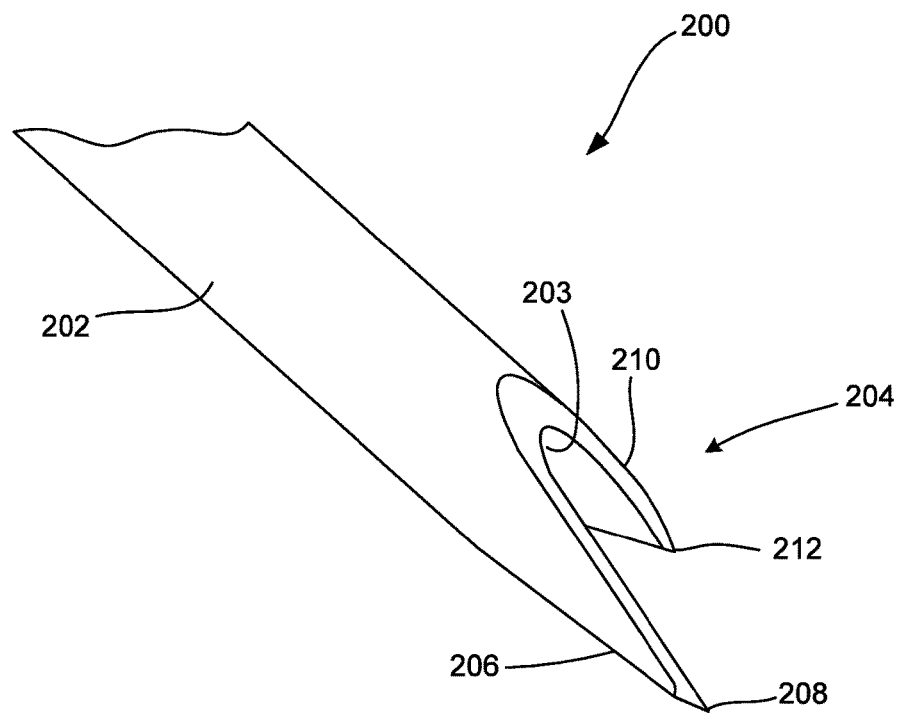
FIG. 3 is a perspective view of a portion of a biopsy needle consistent with the present disclosure.
Figure 4:
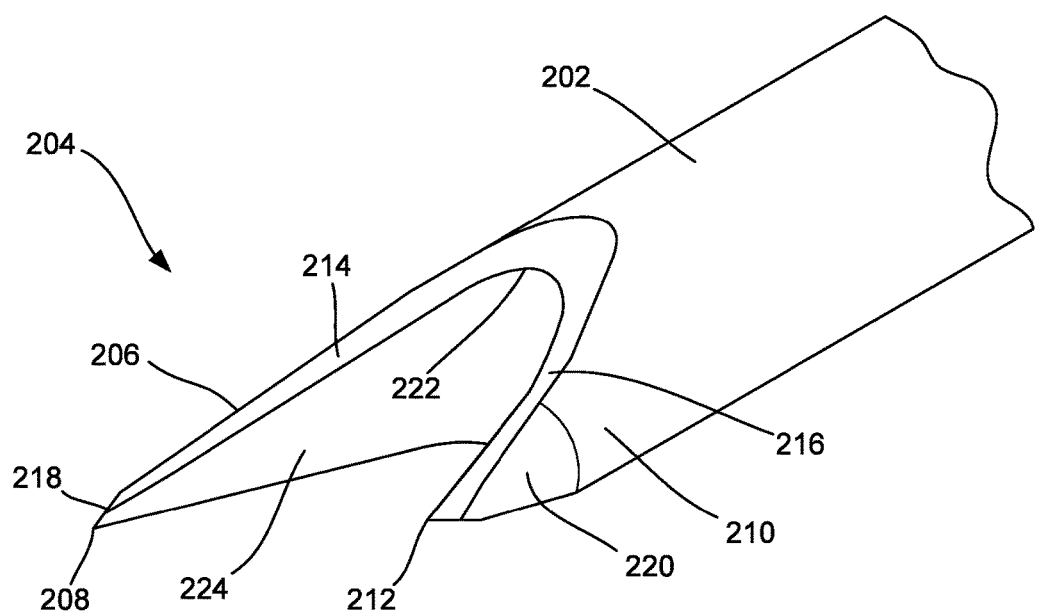
FIG. 4 is a perspective view of a portion of a biopsy needle consistent with the present disclosure.

FIGS. 3 and 4 show a distal portion a biopsy needle 200 consistent with the present disclosure. As shown, the needle 200 generally includes an elongate tubular body 202 having a lumen 203 extending through the body 202 from a proximal open end (not shown) to a distal open end 204. The distal end 204 is configured for collection and harvesting of a sample, including, but not limited to, tissue, fluid, and/or cell samples. In particular, the distal end 204 is beveled in a distinct configuration so as to enhance the ability of the needle 200 to penetrate and collect tissue during sample acquisition.

The distal end 204 includes a first tip portion 206 and a second tip portion 210 extending therefrom, wherein the first and second tip portions 206, 210 are formed on opposing sides of the needle body 202, such that the tip portions radially oppose one another. The first and second tip portions 206, 210 each include a point 208, 212, respectively. The points 208, 212 are configured to penetrate a tissue sample, with relatively little or no resistance during tissue sampling procedure and further configured to direct tissue towards the lumen 203 of the body 202.

The first tip portion 206 is generally formed from at least a first bevel 214 grind (shown on one side of the needle body 202) and the second tip portion 210 is formed from at least a second bevel grind 216, wherein the first and second bevel grinds 214, 216 are different from one another. The differing bevel grinds 214, 216 result in different lengths of the first and second tip portions 206, 210. For example, the first tip portion 206 has a length $L_1$ and the second tip portion 210 has a length $L_2$. The lengths $L_1$ and $L_2$ are each measured from an apex of an arcuate cutting edge shared between the first and second tip portions 206, 210 (shown in FIG. 6) and the corresponding tips 208, 212. In the illustrated embodiment, $L_1$ is greater than $L_2$, such that the first tip portion 206 is essentially longer and extends further from apex than the second tip portion 210, such that the first and second tip portions 206, 210 are in a staggered configuration. As such, the first tip portion 206 is configured to contact and engage tissue to be sampled prior to contact and engagement of tissue by the second tip portion 210, which provides associated benefits, as will be described in greater detail herein. In some embodiments, at least one of the first and second tip portions 206, 210 includes a back-cut grind 218, 220 adjacent the respective point 208, 212. Among other benefits, the back-cut grind 218, 220 is configured to provide a smooth needle passage during needle insertion and withdrawal during a biopsy procedure, described in greater detail herein.

The distal end 204 further includes at least one curvilinear, or arcuate, cutting edge 222 extending between the first tip portion 206 and the second tip portion 210. The cutting edge 222 is generally formed by the first and second bevel grinds 214, 216 of the first and second tip portions 206, 210. During a tissue collection procedure, the cutting edge 222 is configured to excise tissue upon contact therewith and further allow the excised tissue sample to translate into the lumen 203 and contact the internal surface 224 of the lumen 203 for harvesting.

Figure 5:
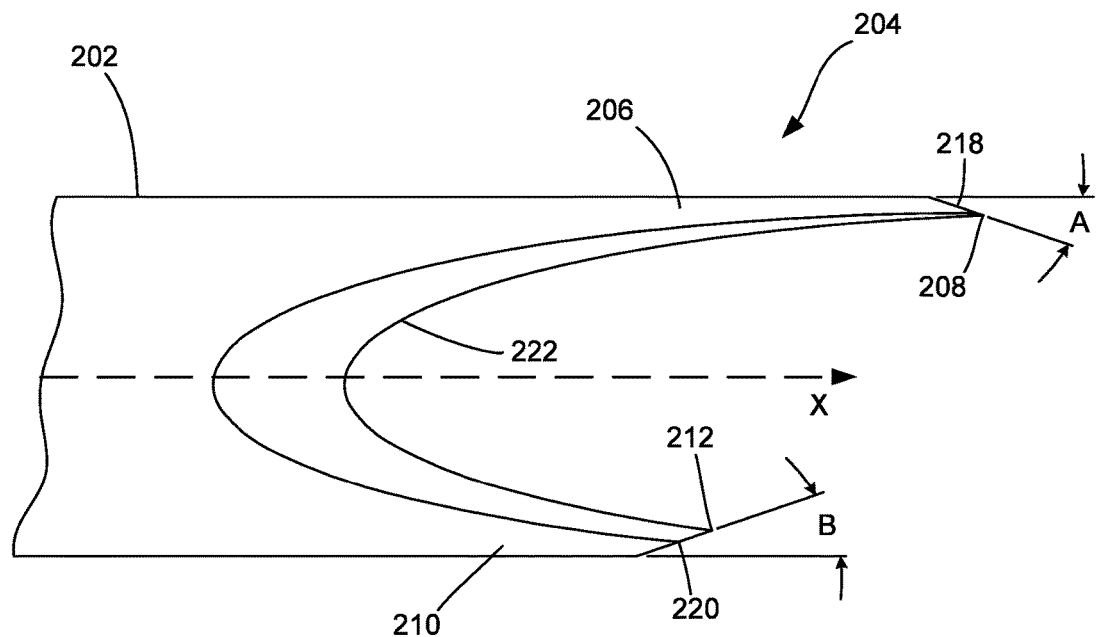
FIG. 5 is an enlarged side profile view of the distal end of the biopsy needle of FIGS. 3 and 4.

FIG. 5 is an enlarged side profile view of the distal end 204 of the biopsy needle 200. As shown, the cutting edge 222 generally extends entirely from the point 208 of the first tip portion 206 to the point 212 of the second tip portion 210. However, it should be noted that in other embodiments, the cutting edge 222 may only partially extend between distinct portions of the first and second tip portions 206, 210. In one embodiment, at least one of the first and second tip portions 206, 210 includes a back-cut grind. In another embodiment, i.e., as shown in the figures, both the first and second tip portions 206, 210 include a back-cut grind 218, 220, respectively. Each back-cut grind 218, 220 includes a back-cut angle oblique to an outer surface of the needle body 202. For example, back-cut grind 218 has a back-cut angle A and back-cut grind 220 has a back-cut angle B, wherein angles A and B are in the range of 15 degrees to 70 degrees, but more preferably in the range of 25 degrees to 45 degrees. In one embodiment, the back cut angles A and B are 30 degrees.

The inclusion of at least back-cut grind 218 on the first tip portion 206 may ensure the smooth passage of the needle down a sheath, or other enclosure of a delivery device, during needle movement and/or exchange. For example, the biopsy needle 200 of the present disclosure may be used in conjunction with a delivery device, such as an endoscopic device for delivering the needle 200 to the target site for tissue collection. The endoscopic device may generally include a sheath, or other enclosure, for provide the needle 200 with access to a target site for tissue collection. As such, during a needle exchange, for example, it is important that the needle 200 can be passed through an internal diameter of a sheath of the delivery device without catching on an internal wall of the sheath. As the needle advances, the heel of the back-cut grind 218 may come in contact with the internal diameter of the sheath and reduce the friction between the distal end 204 of the needle 200, particularly the point 208 of the first tip portion 206, and the sheath. In this way, the needle 200 can be smoothly tracked through the sheath to exit the end of the sheath. This feature also makes it easy to remove a needle and re-insert a new needle while the rest of a delivery device remains within a patient during a procedure.

Figure 6:
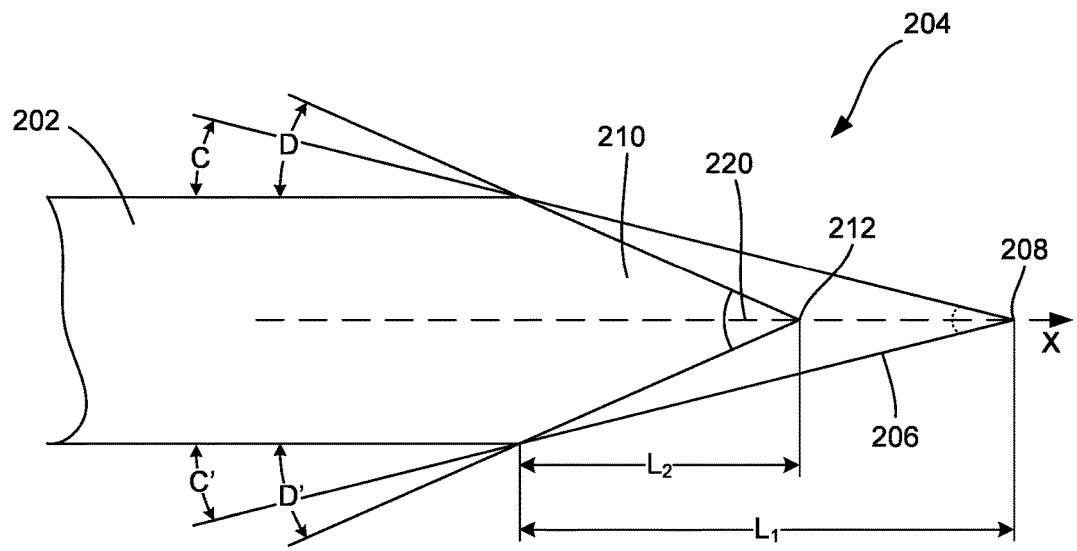
FIG. 6 is a bottom view of the distal end of the biopsy needle of FIGS. 3 and 4.

FIG. 6 is a bottom view of the distal end 204 of the biopsy needle 200 illustrating sets of bevel grinds that form the distal end 204. As shown, the first and second tip portions 206, 210 are formed from first and second sets of distinct angular bevel grinds that enhance tissue penetration and collection. For example, the first tip portion 206 is formed from a first set of distinct angular bevel grinds oblique to the longitudinal axis X of the needle body 202. The first set of angular bevel grinds comprises at least a first angle C on one side of the body 202 and a second angle C' on the opposing side of the body 202, wherein both angles C and C' are oblique to the longitudinal axis X of the body 202. In one embodiment, angles C and C' may be the same. In other embodiments, angles C and C' may be different. The first and second angles C and C' are in the range of 5 to 40 degrees. In some embodiments, the first and second angles C and C' are in the range of 5 to 20 degrees. In one embodiment, the first and second angles C and C' are 15 degrees.

Similarly, the second tip portion 210 is formed from a second set of distinct angular bevel grinds oblique to the longitudinal axis X of the needle body 202. The second set of angular bevel grinds comprises at least a third angle D on one side of the body 202 and a fourth angle D' on the opposing side of the body 202, wherein both angles D and D' are oblique to the longitudinal axis X of the body 202. In one embodiment, angles D and D' may be the same. In other embodiments, angles D and D' may be different. The third and fourth angles D and D' are in the range of 15 to 40 degrees. In some embodiments, the third and fourth angles D and D' are in the range of 20 to 30 degrees. In one embodiment, the third and fourth angles D and D' are 25 degrees.

In the illustrated embodiment, the first and second sets of angular bevel grinds are different than one another. For example, in one embodiment, the first and second angles C and C' (forming the first tip portion 206) are approximately 15 degrees and the third and fourth angles D and D' (forming the second tip portion 210) are approximately 25 degrees. Accordingly, the first and second angles C and C' are less than the third and fourth angles D and D', resulting in the first and second tip portions 206, 210 having different associated lengths. For example, the first tip portion 206 has a length $L_1$ (measured from the tip 208 to an apex of the arcuate cutting edge 222) and the second tip portion 210 has a length $L_2$ (measured from the tip 212 to an apex of the arcuate cutting edge 222), wherein $L_1$ is greater than $L_2$. Accordingly, the first tip portion 206 is longer and extends further from the distal end 204 than the second tip portion 210, such that the first and second tip portions 206, 210 are in a staggered configuration and the first tip portion 206 leads during tissue collection. More specifically, the first tip portion 206 is configured to contact and engage tissue to be sampled prior to contact and engagement of tissue by the second tip portion 210. The lengths $L_1$ and $L_2$ of the first and second tip portions 206, 210 are in the range of 0.5 to 5 mm. In some embodiments, the length $L_1$ is in the range of 2 to 3 mm and the length $L_2$ is in the range of 0.5 to 1.5 mm. In one embodiment, the first tip portion 206 has a length $L_1$ of approximately 2.0618 mm and the second tip portion 210 has a length $L_2$ of approximately 1.3 mm. It should be noted that the first and second sets of angular bevel grinds may be manipulated so as to result in adjustment of lengths $L_1$ and $L_2$ of the first and second tip portions, respectively.

Figure 1:
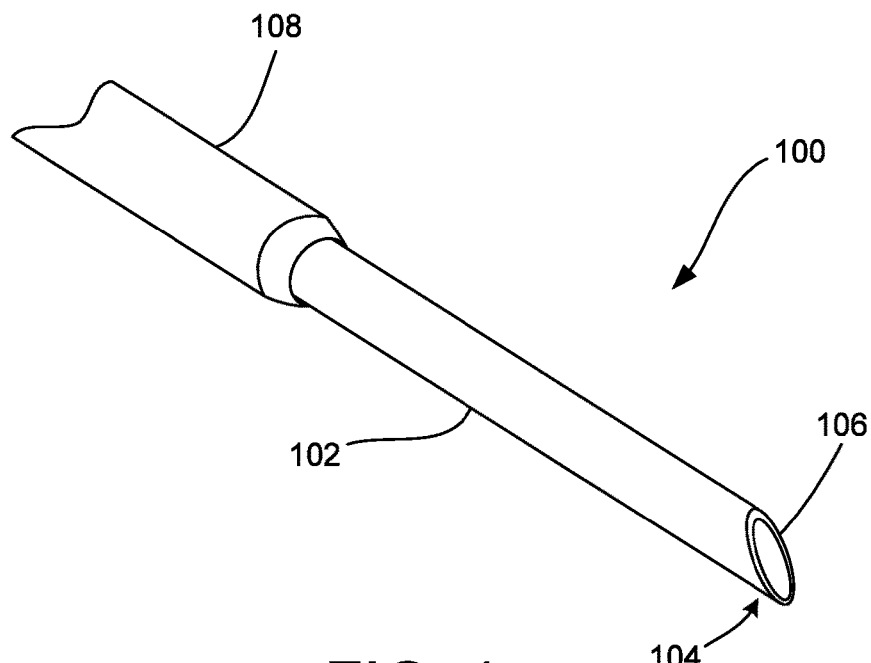
FIG. 1 is a perspective view of an embodiment of a biopsy needle known in the art.
Figure 2:
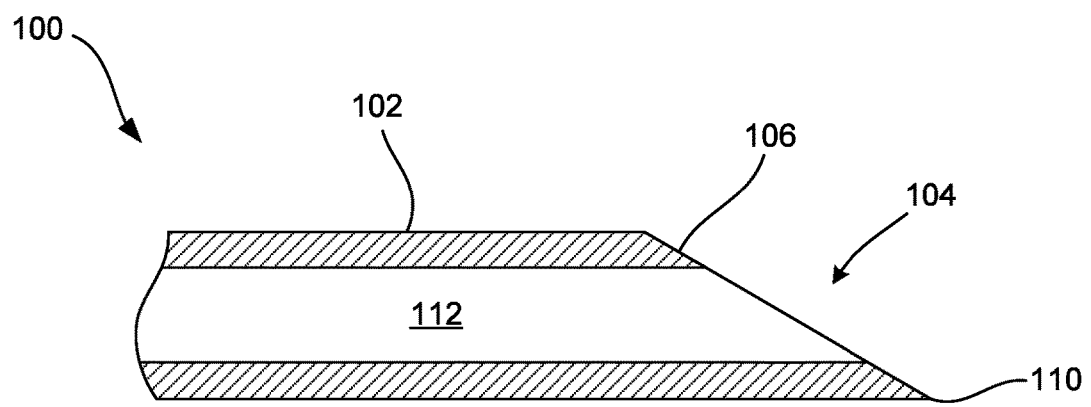
FIG. 2 is a cross-sectional view of the biopsy needle of FIG. 1.

The distinct configuration of the distal end 204 of the biopsy needle 200 is configured to maximize tissue sampling yield and further ensure collection of a cohesive unit of sampled tissue, thereby overcoming the drawbacks of current biopsy needles (such as needle 100 of FIGS. 1 and 2). For example, by providing a staggered configuration of the first and second tip portions 206, 210, the surface area of the effective cutting edge 222 is increased when compared to beveled leading distal ends pf current biopsy needles (e.g., Menghini, Franseen, Quicke, etc.). Additionally, because the first tip portion 206 is longer than the second tip portion 210, the first tip portion 206 is configured to initially pierce the tissue to be sampled with little or no resistance and further guide the sample tissue into the lumen 203 of the biopsy needle 200. If the first and second tip portions 206, 210 were of equal length, it may prove more difficult to initially puncture of tissue sample, particularly a fibrous tissue. Furthermore, as the tissue is guided toward the lumen 203, second tip portion 210 is further configured to capture and lead additional tissue towards the lumen 203 to be excised by the cutting edge 222 upon contact therewith. By increasing the effective cutting surface area and having the staggered configuration of first and second tip portions 206, 210, the biopsy needle 200 of the present disclosure is able to guide tissue into the lumen in a controlled manner and maximize the amount of tissue harvested, particularly upon aspiration.

Figure 7:
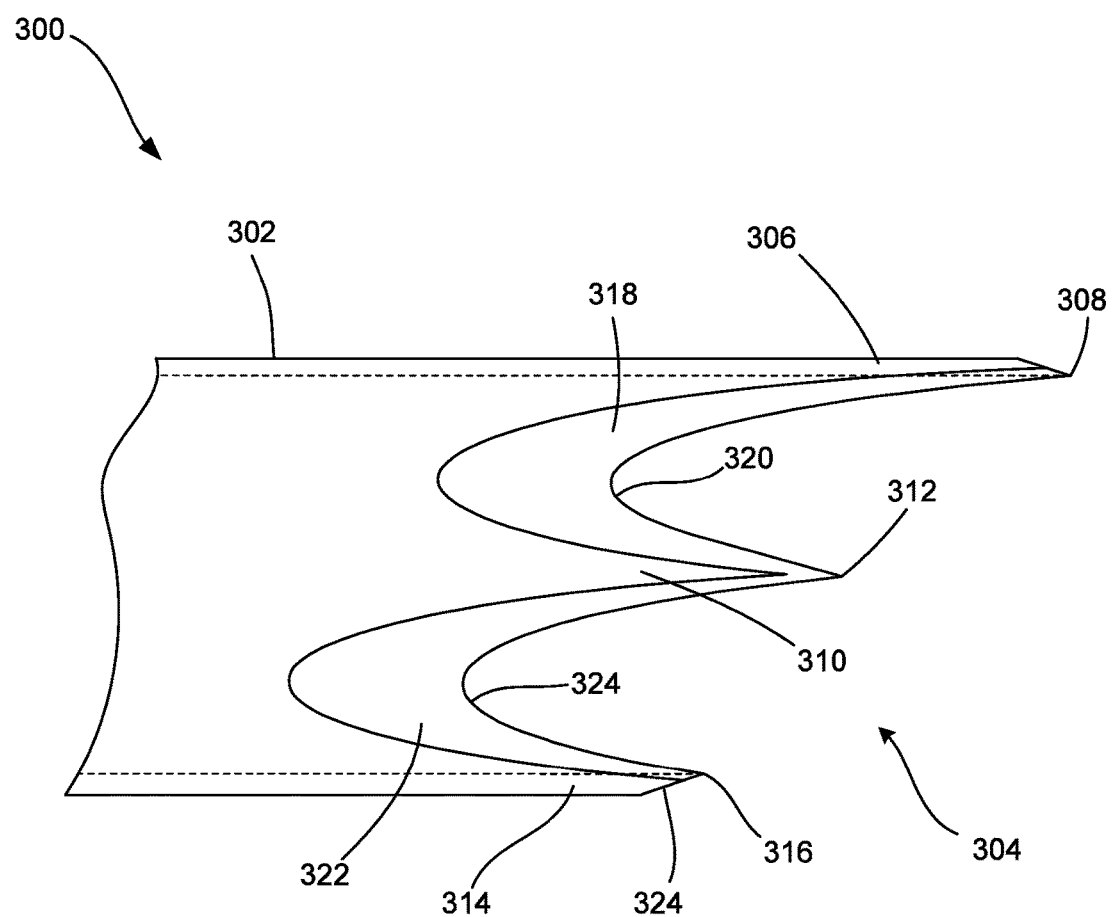
FIG. 7 is an enlarged side profile view of an alternative embodiment of a distal end of a biopsy needle consistent with the present disclosure.

It should be noted that a biopsy needle consistent with the present disclosure is not limited to the number of tip portions (e.g., two tip portions). For example, FIG. 7 is an enlarged side profile view of an alternative embodiment of a distal end 304 of a biopsy needle 300 having at least four tip portions extending from the distal end. As shown, the needle 300 may include first and second tip portions 306, 314 (similar to needle 200), and an additional third 310 and fourth (not shown) tip portion formed between the first and second tip portions 306, 314, wherein the first and second tip portions 306, 314 radially oppose one another on either side of the needle body 302 and the third and fourth tip portions radially oppose one another on either side of the needle body 302. As shown, the first tip portion 306 is longer than the third (and fourth) tip portion 310, which is longer than the second tip portion 314, such that distal end 304 maintains a staggered configuration. The inclusion of additional tip portions may further increase the surface area of cutting edges 320, 324 formed between the tip portions, which may be particularly beneficial when sampling certain types of tissue that may prove to be tough or resistant to cutting (e.g., fibrous tissue).

The biopsy needle of the present disclosure may be used in conjunction with minimally-invasive procedures, such as endoscopic procedures. For example, the biopsy needle may be compatible with an endoscopic biopsy device, such as needle biopsy delivery device configured for endoscopic ultrasound or endoscopic bronchial ultrasound procedures. For example, the biopsy needle may be compatible for use with exemplary endoscopic deliver systems and methods discussed in Needle Biopsy Device with Exchangeable Needle and Integrated Needle Protection, U.S. Pub. 2012/0116248, Rapid Exchange FNA Biopsy Device with Diagnostic and Therapeutic Capabilities, U.S. Pub. 2011/0190662, Device for Needle Biopsy with Integrated Needle Protection, U.S. Pub. 2010/0121218, and Needle Biopsy Device, U.S. Pub. 2010/0081965, the contents of each of which are hereby incorporated by reference in their entirety.

Figure 8:
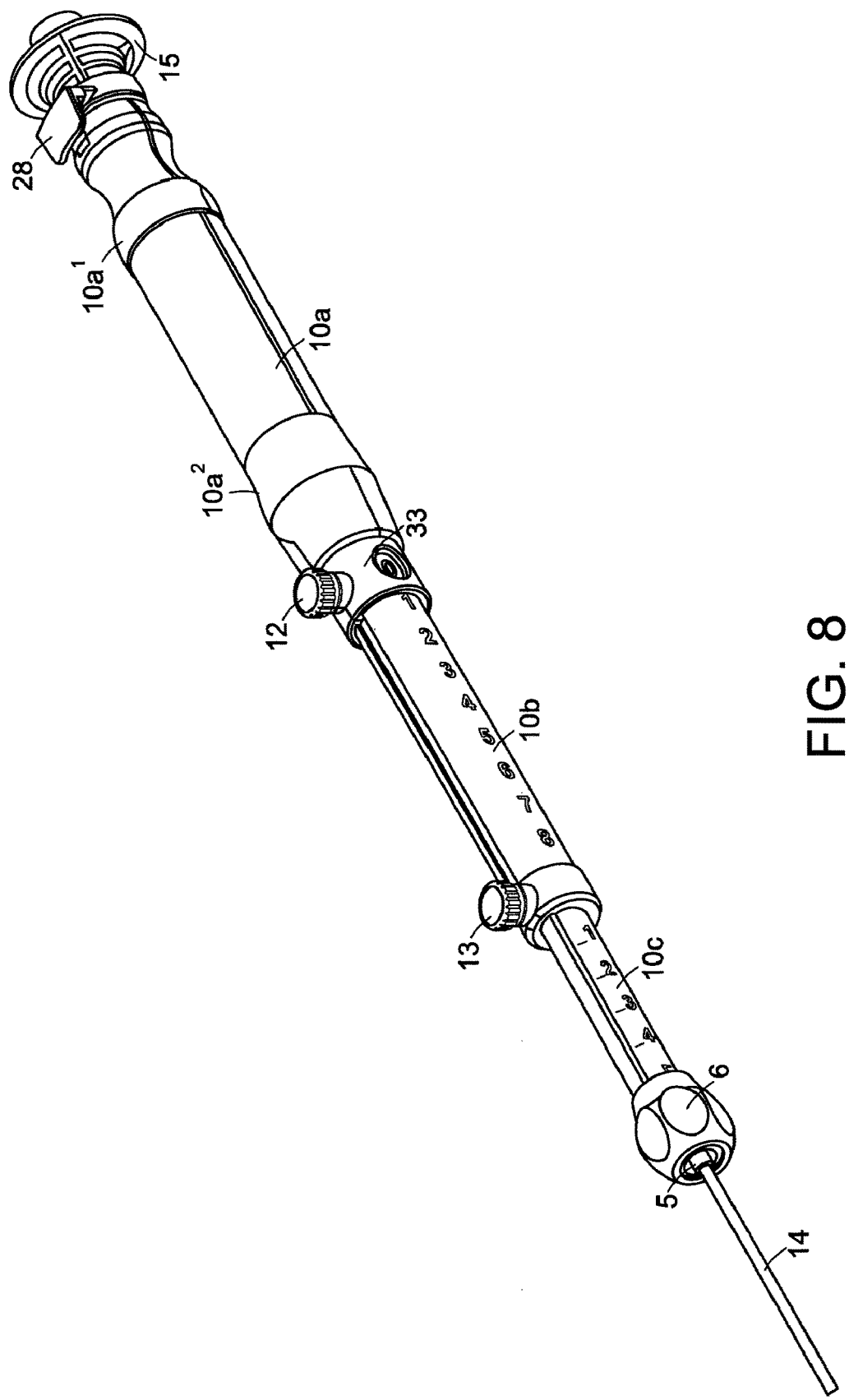
FIG. 8 is a perspective view of a biopsy device including an adjustable delivery handle and sheath for receipt of and use with an exchangeable biopsy needle consistent with the present disclosure.

An exemplary embodiment of an endoscopic delivery device assembly for use with a biopsy needle of the present disclosure is illustrated in FIG. 8. The device and specific delivery methods are discussed in more detail in Needle Biopsy Device with Exchangeable Needle and Integrated Needle Protection, U.S. Pub. 2012/0116248, the contents of which are hereby incorporated by reference in their entirety. The device design consists of a handle mechanism (delivery system handle 10) and removable needle sub-assembly 15. The delivery system handle 10 includes a proximal handle member 10a, a middle handle member 10b, and a distal handle member 10c. The proximal, middle and distal handle members each include an inner lumen and are coupled together to define a longitudinal axis such that the inner lumens are in constant communication and extends throughout the length of the coupled handle members. Proximal handle member 10a is slideably disposed over at least a portion of the middle handle member 10b, and middle handle member 10b is slideably disposed over at least a portion of distal handle member 10c. The proximal handle member 10a includes proximal handle grip 10a1 a distal handle grip 10a2. The delivery handle system 10 further includes an inner handle member 10d disposed within the inner lumen of the middle handle member 10b.

The delivery system handle 10 also incorporates a sheath 14 component coupled to the distal end of the distal handle member 10c. This component provides a conduit between the delivery system handle 10 and the target sampling site during the exchange of needles, such as the biopsy needle previously described herein. The device design is modular in that the needle sub-assembly 15 can be detached from the proximal handle 10a of the device for each individual "pass" or aspirated sample taken by the endoscopist at the site of the lesion or abnormality.

The delivery system handle 10 incorporates two length adjustment features actuated via adjustment of two thumb-screw locking mechanisms. A threaded proximal thumbscrew 12 and locking ring 33 are moveably disposed around the middle handle member 10b, the proximal thumbscrew 12 is loosened to loosen locking ring 33, locking ring 33 is moved distally along the middle handle member 10b and tightened in the desired position along middle handle member 10b via proximal thumbscrew 12 to allow the user to establish a set depth of needle penetration beyond the end of the sheath 14. A threaded distal thumbscrew 13 is transversely disposed at the distal portion of the middle handle member 10b, the distal thumbscrew 13 is loosened to move the middle handle member 10b distally and/or proximally and tightened to allow the user to establish a set depth of sheath 14 extension beyond the end of the endoscope accessory channel.

The needle sub-assembly 15 consists of at least a biopsy needle consistent with the present disclosure (e.g., needle 200). The body 202 of needle 200 can range in length from 200 mm up to 2500 mm. In some embodiments, the needle body 202 can range in length between 500 mm to 2000 mm. In some embodiments, the needle body 202 can range in length between 800 mm to 1800 mm. In some embodiments, the needle body 202 can range in length between 1640 mm to 1680 mm. The needle sub-assembly 15 further includes needle hub 17, needle luer 18, needle collet 226, needle protector sub-assembly 9, stylet hub 20, and stylet shaft 22.

As generally understood, the needle 200 itself can be manufactured from a variety of metallic based materials, including, but not limited to, nitinol, cobalt chrome, stainless steel, a metal alloy, combinations thereof, or Polymeric Based materials including, but not limited to poly-ether-ether ketone, polyamide, poyethersulfone, polyurethane, ether block amide copolymers, polyacetal, polytetrafluoroethylene and/or derivatives thereof. It should be noted that the biopsy needle is not limited to any particular gauge (e.g., outer diameter). For example, depending on the type of sample to be collected, as well as the target site from which the sample is to be collected, the biopsy needle may range from 10-gauge to 30-gauge, and more specifically 15-gauge to 28-gauge, i.e., gauge 12, 14, 15, 16, 17, 18, 19, 20, 21, 22, 23, 24, or 25 needles.

Figure 9:
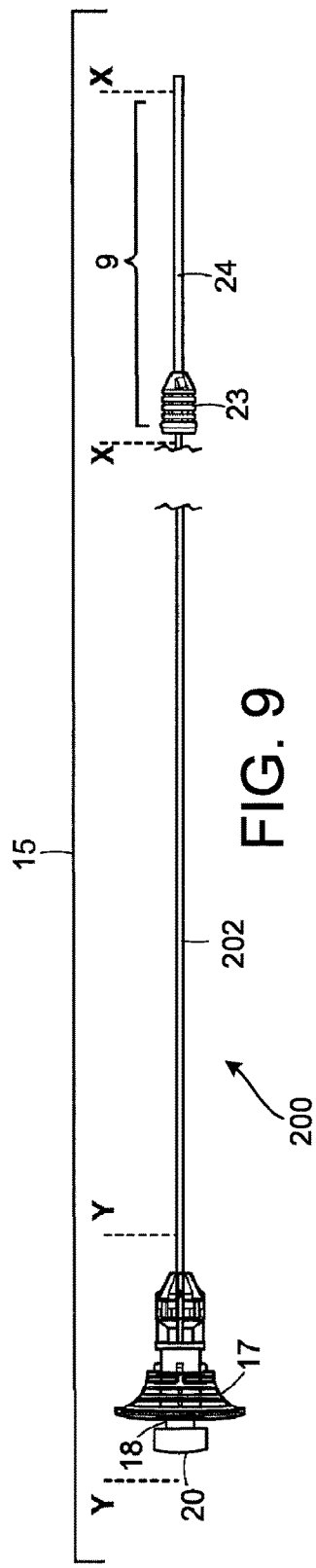
FIG. 9 is a drawing of the needle sub-assembly of the device of FIG. 8.

FIG. 9 is a drawing of the needle sub-assembly 15 of the device of FIG. 8. The sub-assembly 15 is inserted into and removed from the lumen of the delivery system handle 10 in acquiring tissue samples. The sub-assembly 15 consists of stylet hub 20 and stylet shaft 22 components which are securely locked on the needle luer 18 of the needle 200 via conventional internal luer threads, as generally understood by one skilled in the art. The stylet hub 20 may be attached to the stylet shaft 22 via any known processing techniques, including, but not limited to, adhesive bonding or insert injection molding. The female luer of the needle 200 incorporates a mating luer thread detail, onto which the stylet hub 20 may be tightened. The needle luer 18 element of the present disclosure may be attached to the proximal end of the needle shaft via a number of processing techniques such as adhesive bonding or insert injection molding.

The removable needle sub-assembly 15 also incorporates a needle collet 226. The function of this needle collet 226 is to provide a means to center the needle body 202 in the sheath 14 of the delivery system during needle exchange and provide a mechanism for securing and locking the needle protector sub-assembly to the distal end 204 needle 200 once the needle 200 has been unlocked and withdrawn from the delivery system handle. The needle collet 226 of the present disclosure may be attached to a portion of the needle body 202 near the distal end 204 of the needle 200 by way of any known processing techniques, including, but not limited to, adhesive bonding, laser welding, resistance welding, insert injection molding, and combinations thereof. The needle collet 226 may be fabricated from metals materials such as stainless steel, nickel titanium or alloys thereof or polymer materials such as, but not limited to, Polyacetal, polyamide, poly-ether-block-amide, polystyrene, Acrylonitrile butadiene styrene or derivatives thereof.

Figure 10:
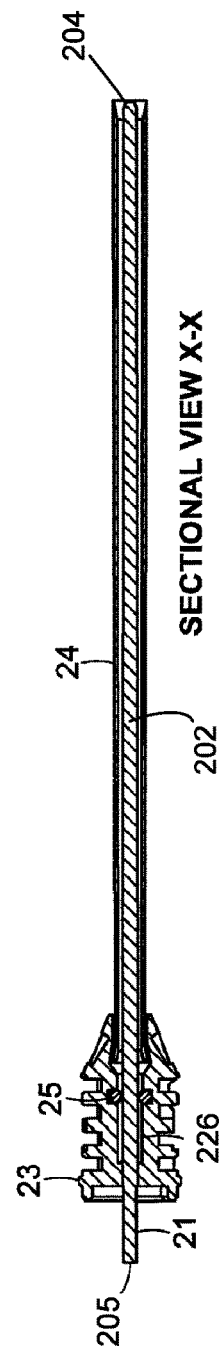
FIG. 10 is a cross sectional drawing of the needle protector embodiment of the needle sub-assembly of FIG. 9.

FIG. 10 illustrates the needle protection sub-assembly 9 design embodiment of the present disclosure in the locked position at the distal end 204 of the needle 200. The needle protection sub-assembly 9 consists of two needle protector (NP) hub halves (collectively 23), which are adhesively bonded to each other, on the proximal end of the needle protector (NP) sheath component 24. Alternatively, the NP hub halves 23 may be snap fit together or may be insert injection molded over the NP sheath 24 to provide a secure bond/attachment between these components in the assembly. The needle protection sub-assembly 9 also incorporates a needle protector (NP) hub O-Ring component 25. The O-Ring component resides in a recessed cut-out in the center of the assembled NP hub halves 23. The NP hub O-Ring 25, in conjunction with the needle collet 226, which is securely attached to a portion of the needle body 202 near the distal end 204 of the needle 200, provides a mechanism for locking the NP sub-assembly 9 onto the end of the needle 200. In this way, the distal cutting end 204, including the first and second tip portions 206, 210 previously described herein, is protected, covered and shielded once the needle has been removed from the delivery system handle. For example, upon acquiring a sample from a target site, the needle 200 may be removed so as to gain access to the sampled material for testing and diagnostic procedures. The needle 200 may be continually withdrawn from the delivery system handle 10, such that the needle collet 226 contacts the NP hub O-ring 25 and further pulls the NP sub-assembly 9 from engagement with needle hub 17, such that the needle 200 is completely removed from the delivery system handle 10 and the NP sheath 24 encases the distal end 204 of the needle 200 to prevent inadvertent "needle sticking". Further, an operator may then pull back the NP sub-assembly 9 from the distal end 204 of the needle 200 so as to collect the sampled material stored within the lumen of the needle 200. Accordingly, the NP sub-assembly 9 is configured to translate along a length of the needle 200 so as to allow access to the distal end 204 of the needle 200 post acquisition and when the needle 200 is entirely removed from the delivery system handle 10.

Figure 11:
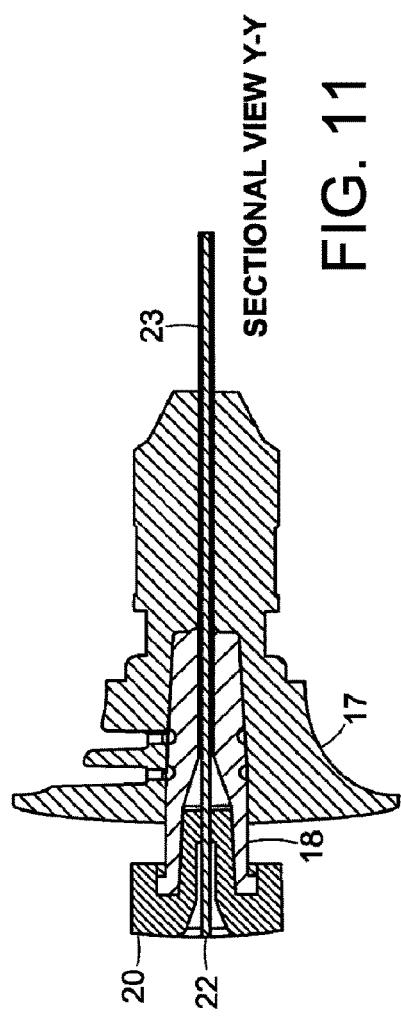
FIG. 11 is a cross sectional drawing of the needle hub at the proximal end of the biopsy needle sub-assembly of FIG. 9.

Referring the FIG. 11, the needle hub 17 embodiment of the needle sub-assembly is generally illustrated. The needle hub 17 provides a mechanism configured to lock the removable needle sub-assembly 15 into the delivery system handle 10 by means of the hub housing 27 and thumb latch 28 components and provide a means to lock the needle protection sub-assembly 9 embodiment shown in FIG. 10, into the delivery system device handle 10. As shown in FIG. 11, the needle hub component 17 is securely attached to the needle luer 18 and needle body 202. The needle hub element 17 of the present disclosure may be attached to the distal end of the needle luer component 18 via a number of processing techniques such as adhesive bonding or insert injection molding.

In some instances, it may be preferable to switch needles during a procedure, while still maintaining access to the target site. The delivery system of FIG. 8 is configured to allow rapid needle exchanges without requiring the delivery system to be removed from the scope, as described in greater detail in U.S. Pub. 2012/0116248, the contents of which are hereby incorporated by reference in their entirety. Accordingly, the sheath 14 may remain at a target site for an indefinite period of time while allowing the exchange of multiple needles. The rapid needle exchange capabilities provided by the delivery system of the present disclosure may further decrease the amount of time required for a biopsy procedure, which may cut down the amount of anesthesia required during a particular procedure, improving patient safety. Additionally, a new biopsy device is not required for each needle, as may be the case with current biopsy devices and techniques. Accordingly, the delivery system and exchangeable needles of the present disclosure can cut down on costs and by preventing unnecessary waste.

Figure 12:
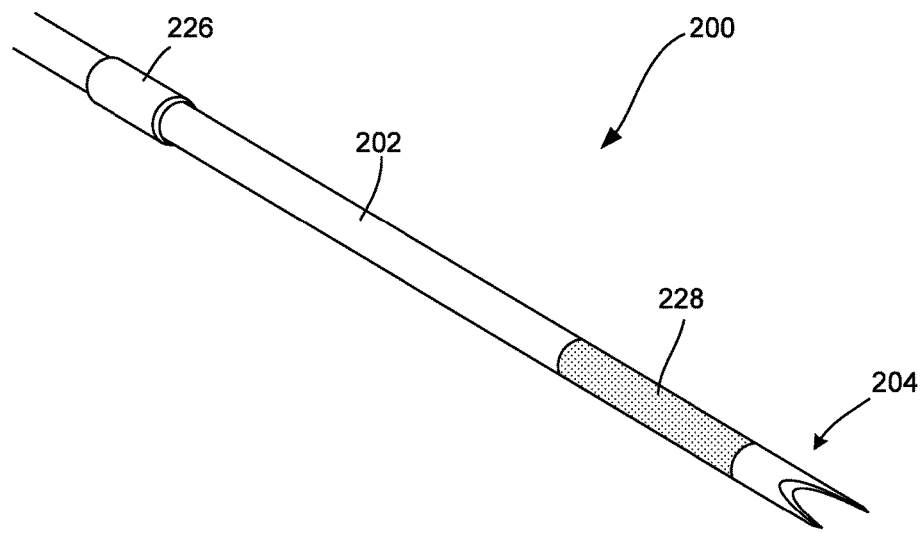
FIG. 12 is a perspective view of a biopsy needle consistent with the present disclosure.

FIG. 12 is a perspective view of a portion of the biopsy needle near the distal end. As shown, the needle 200 further includes collet 226 coupled to a portion of the needle body 202. The length of the needle collet 226 may be in the range of 2 mm to 10 mm, but more preferably in the range of 3.5 mm to 5 mm. It is preferable that the outer diameter of the needle collet 226 be in the range of 0.030 inches to 0.080 inches, but more preferably in the range of 0.040 inches to 0.070 inches, depending on the gauge of the needle 200. The needle collet component 226 may be chamfered at the proximal and distal ends thereof. In some embodiments, it may be preferable that the chamfer angle of the needle collet 226 be in the range of 15 degrees to 80 degrees, oblique to a longitudinal axis of the needle 200, but more preferably in the range of 30 degrees to 60 degrees. The chamfer on both ends of the needle collet 220 may provide smooth locking and unlocking with the needle protector sub-assembly 9 during needle exchanges.

The needle collet 226 is located at a set point distance from the distal end 204 of the needle 200. The distance from the distal end 204 of the needle to the proximal collet position on the needle 200 may be within the range of 6 cm to 12 cm, but is more preferably in the range of 7 cm to 9 cm, and more preferably is located 8 cm from the end of the needle 200. This ensures that when the needle is extended to a maximum extension distance relative to the distal end 14*a* of the sheath (i.e. 8 cm), the collet 226 does not exit the end of sheath 14, as shown in FIGS. 13A and 13B.

In the illustrated embodiment, a portion 228 of the needle body 202 adjacent the distal end 204 may incorporate an embodiment to enhance the echogenic signature of the needle 200. For example, this echogenically enhanced region 228 can be fabricated by, but not limited to, roughening the end of the needle over a pre-defined length adjacent to at least the first and second tip portions of the distal end 204. The length of the echogenically enhanced region 228 may be in the range of 2 mm to 20 mm, but is more preferably in the range of 10 mm to 15 mm. The echogenic enhanced pattern 228 may be imparted to the needle body 202 via a micro-blasting process which roughens the surface of the needle over a specific length, improving the visibility of the needle under endoscopic ultrasound. In other embodiments, the echogenically enhanced region 228 of the needle 200 may be achieved through the removal of material from the surface of the needle to provide greater reflectivity and strengthened reflected signal. It is contemplated that the removal of material does not, however, reduce the performance of the needle from a pushability perspective or deter its ability to acquire a desired sample.

Figure 13A:
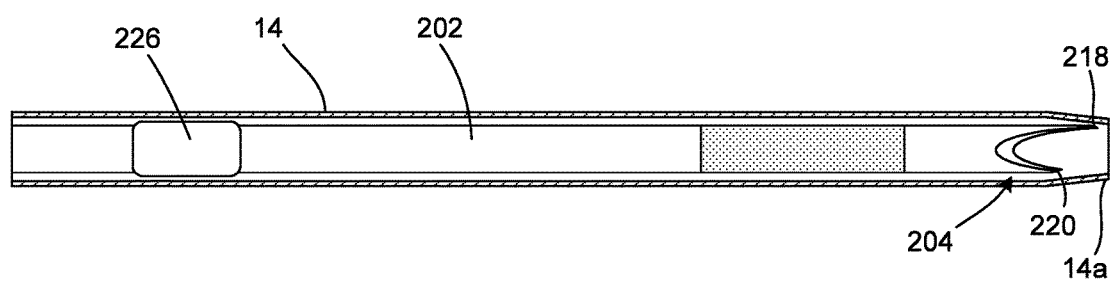
FIG. 13A is a side view, partly in section, of storage of the biopsy needle of FIG. 12 within the sheath of FIG. 8.
Figure 13B:
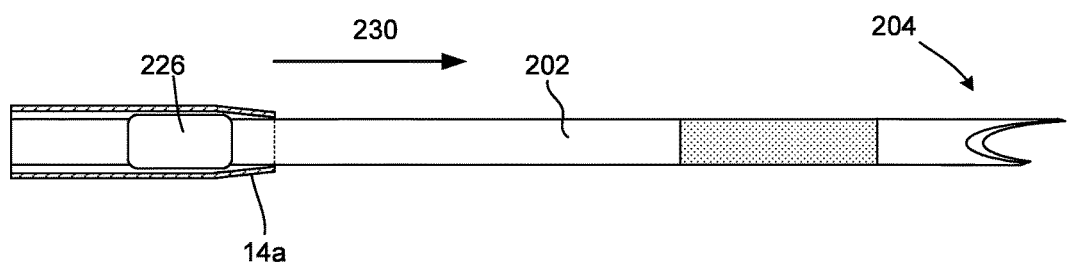
FIG. 13B is a side view, partly in section, of extension of the biopsy needle of FIG. 12 from the sheath of FIG. 8.

FIGS. 13A and 13B are side views, partly in section, of storage and extension of the biopsy needle 200 of FIG. 12 within the sheath 14 of the delivery system of FIG. 8. Referring to FIG. 13A, the needle 200 is shown loaded within the sheath 14 with the device handle in the fully retracted position and ready for extension into a target site for sample collection. In this instance, the distal end 204 of the needle 200 lies proximal to the distal tapered end 14*a* of the sheath 14. FIG. 13B illustrates the position of the needle 200 and needle collet 226 relative the sheath 14 when the needle transitions to a fully extended position, as indicated by arrow 230. In the fully extended position, the needle collet 226 remains housed inside sheath 14, proximal to the tapered distal tip, thereby preventing the needle 200 from extending past a set distance from the sheath 14.

It is important, particularly during tissue collection procedures and/or needle exchange, that the needle 200 can be passed through an internal diameter of a sheath 14 of the delivery device without catching on an internal wall of same. As the needle advances, the heel of the back-cut grind 218 on the first tip portion 206, for example, may come in contact with the internal diameter of the sheath 14 and reduce the friction between the distal end 204 of the needle 200, particularly the point 208 of the first tip portion 206, and the sheath 14. In this way, the needle 200 can be smoothly tracked through the sheath to exit the end of the sheath.

Figure 14:
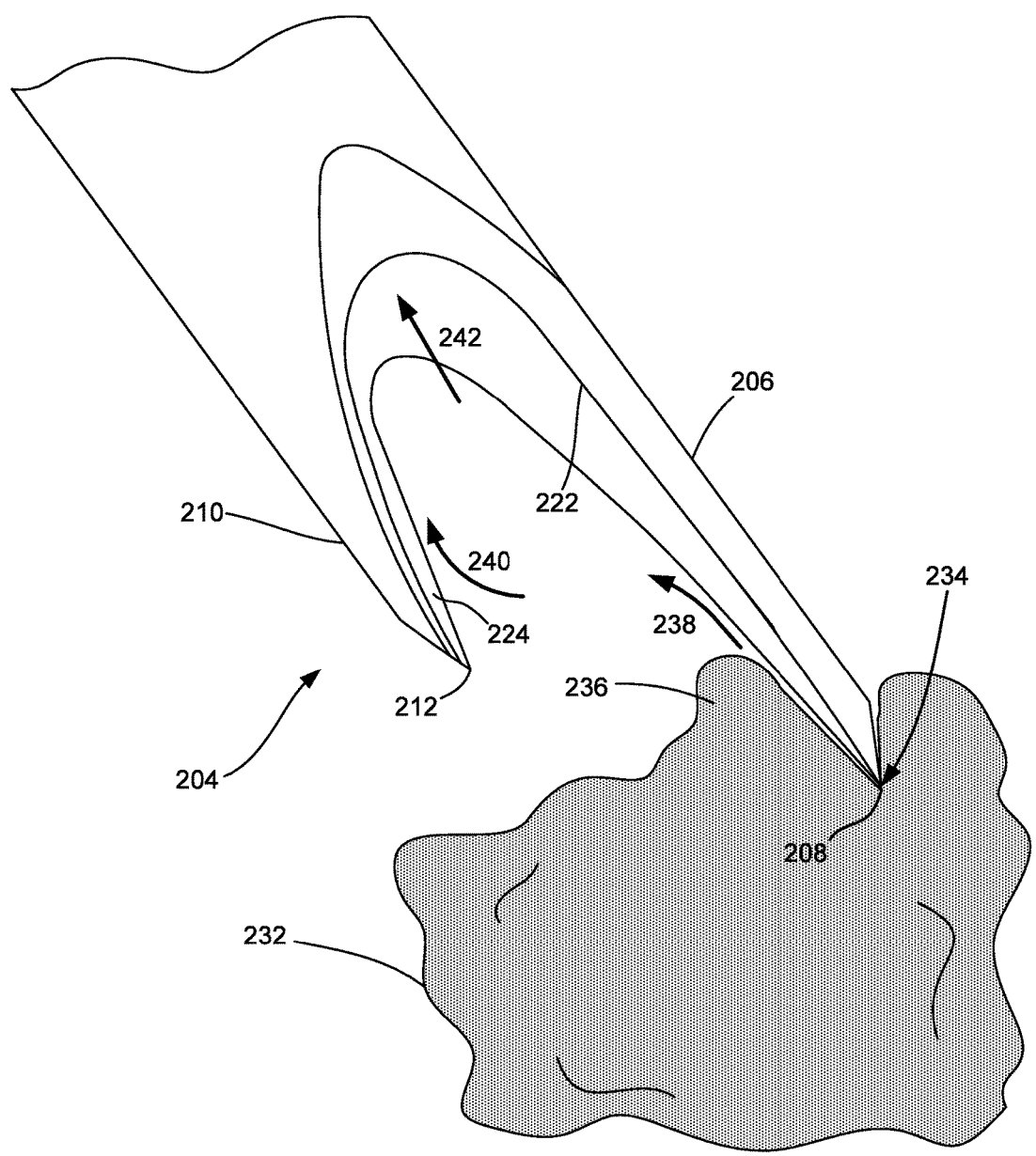
FIG. 14 is a perspective view illustrating the initiation of sample tissue collection with a biopsy needle consistent with the present disclosure.

FIG. 14 is a perspective view illustrating the initiation of sample tissue collection with a biopsy needle 200. As shown, the needle 200 may be extended from the sheath 14 when delivered to a target site. An operator (e.g., physician or other trained medical personnel) may then advance the distal end 204 of the needle 200 towards the target tissue 232 to be sampled (with or without the assistance of use of ultrasound techniques). As shown, because the first tip portion 206 has a greater overall length than the second tip portion 210, the point 208 of the first tip portion 206 of the distal end 204 contacts and engages the tissue 232, as indicated by arrow 234. The first tip portion 206 is configured to pierce the tissue 232 further direct a tissue sample 236 in a direction towards the lumen 203, as indicated by arrow 238. As the needle is forced further into the target tissue 232, the second tip portion 210, which is set back from the first tip portion 206, is configured to catch and grab additional tissue that may have otherwise deflected off of the first tip portion 206 and may have missed the lumen 203 entirely, as is the case with some current needle tip designs. For example, as tissue is excised by the cutting edge 222 after initial puncture by the tip 208 of the first tip portion 206, the excised tissue may curl away from the first tip portion 208. The shorter second tip portion 210 is then configured to catch and collect the deflected excised tissue, as indicated by arrow 240, and further pierce the target tissue 232, thereby guiding a tissue sample 236 towards the lumen 203 and to be further excised by the cutting edge 22 upon contact therewith, as indicated by arrow 242. In this manner, a full core sample may be achieved. In one embodiment, a vacuum may be communicated from the proximal end to the distal end 204 through the lumen 203 so as to provide a suction force to the target tissue 232 and further assist in collection and harvesting of the tissue sample 238 via aspiration.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A device for needle biopsy comprising:
an adjustable delivery handle system comprising:
a delivery handle, at least a portion of which comprises an inner lumen configured to receive one of a plurality of exchangeable needle subassemblies; and
a sheath coupled to a distal end of the delivery handle and having a lumen in fluid communication with the inner lumen of the delivery handle; and
a needle subassembly removably disposed within the inner lumen of the delivery handle and the lumen of the sheath, the needle subassembly comprising an exchangeable biopsy needle comprising:
an elongate tubular body comprising a lumen extending therethrough from a proximal open end to a distal open end of the body, the distal end comprising a first tip portion extending from the distal end and having a first length and a second tip portion extending from the distal end and having a second length that is less than the first length of the first tip portion, such that the first tip portion is configured to contact and engage tissue to be sampled prior to the second tip portion,
wherein the first tip portion of the needle is formed from first and second angular bevel grinds oblique to the longitudinal axis of the body, wherein the second tip portion of the needle is formed from third and fourth angular bevel grinds oblique to the longitudinal axis of the body, wherein the first and third angular bevel grinds form first and second distinct curved cutting edges on a first side of the body, and wherein the second and fourth angular bevel grinds form third and fourth distinct curved cutting edges on a second side of the body opposite the first side.

2. The device of claim 1, wherein the first and second tip portions of the needle radially oppose one another.

3. The device of claim 2, wherein the first and second angular bevel grinds and the third and fourth angular bevel grinds are different from one another.

4. The device of claim 1, wherein the first, second, third and fourth distinct curved cutting edges are configured to excise tissue upon contact therewith.

5. The device of claim 1, wherein the needle further comprises a collet surrounding a portion of the body and having a diameter sufficient to prevent the body from entirely passing through a distal end of the sheath of the adjustable delivery handle system.

6. The device of claim 5, wherein the needle subassembly further comprises a needle protector subassembly releasably coupled to the collet of the needle.

7. The device of claim 6, wherein the needle protector subassembly comprises a sheath for encasing the distal end of the needle upon withdrawal of the needle from the delivery handle and for preventing inadvertent puncture from at least one of the first and second tip portions of the distal end of the needle.

8. The device of claim 7, wherein the sheath is moveable along a length of the needle and configured to be retracted in a proximal direction to expose the distal end of the needle for removal of acquired tissue sample from the lumen of the needle.

9. The device of claim 6, wherein the needle protector subassembly comprises:

a needle protection hub having a lumen extending therethrough and configured for receiving at least the distal end of the needle;

a deformable O-ring axially disposed within the lumen of the needle protection hub and configured for releasably coupling to the collet of the needle; and a tubular sheath defining a lumen extending from a distal end of the needle protection hub, the lumen of the tubular sheath in communication with the lumen of the needle protection hub for receiving the needle when inserted into the needle protection hub.

10. The device of claim 9, wherein the sheath is configured to encase the distal end of the needle upon withdrawal of the needle from the delivery handle and for preventing inadvertent puncture from at least one of the first and second tip portions of the distal end of the needle.

11. The device of claim 10, wherein the sheath is moveable along a length of the needle and configured to be retracted in a proximal direction to expose the distal end of the needle for removal of acquired tissue sample from the lumen of the needle.

12. The device of claim 1, wherein the lumen of the needle is configured to communicate a vacuum from the proximal end to the distal end of the needle to provide a suction force to the tissue to be sampled.

13. The device of claim 1, wherein each of the first and second tip portions of the needle defines a point configured to pierce the tissue to be sampled and further direct tissue towards the lumen of the needle.

14. The device of claim 1, further comprising a section of the needle adjacent to the distal end and having enhanced echogenicity or acoustic reflection.

15. The device of claim 1, wherein the needle has an outer diameter in the range of 10-gauge to 30-gauge.

16. The device of claim 1, wherein the needle is comprised of a material selected from the group consisting of nitinol, cobalt chrome, stainless steel, a metal alloy, and combinations thereof.

* * * * *